United States Patent [19]

Metz et al.

[11] 4,054,601

[45] Oct. 18, 1977

[54] METHOD OF RECOVERING PURIFIED GLYCOLIC ACID FROM ITS CONTAMINATED AQUEOUS SOLUTIONS

[75] Inventors: Ulrich Metz, Seebruck; Horst Michaud, Trostberg, both of Germany

[73] Assignee: Suddeutsche Kalkstickstoff-Werke Aktiengesellschaft, Trostberg, Germany

[21] Appl. No.: 698,335

[22] Filed: June 22, 1976

[30] Foreign Application Priority Data

July 1, 1975 Germany .............................. 2529170

[51] Int. Cl.$^2$ ............................................. C07C 59/06
[52] U.S. Cl. ................................................. 260/535 R
[58] Field of Search ....................... 260/535 R, 527 R

[56] References Cited

FOREIGN PATENT DOCUMENTS 1,494,958  9/1967  France ........................... 260/527 R Primary Examiner—Paul J. Killos
Attorney, Agent, or Firm—Hans Berman

[57] ABSTRACT

Pure glycolic acid is recovered practically completely from the product obtained by hydrolysis of glycolonitrile containing at least stoichiometrically equivalent amounts of ammonium and sulfate ions by extraction with a mixture of a trialkyl phosphate and a dialkylether, preferably of equal weights of tributyl phosphate and diisopropyl ether, and separation of the glycolic acid from the extraction medium by contact with water.

7 Claims, No Drawings

METHOD OF RECOVERING PURIFIED GLYCOLIC ACID FROM ITS CONTAMINATED AQUEOUS SOLUTIONS

This invention relates to the recovery of glycolic acid from its contaminated, aqueous solutions, and particularly to the recovery of practically pure glycolic acid from the product of glycolonitrile hydrolysis in the presence of sulfuric acid.

It is known from U.S. Pat. No. 1,479,874 to hydrolyze cyanohydrines in the presence of an excess of mineral acid, such as sulfuric acid and chloride ions, to the corresponding hydroxycarboxylic acids. The large excess of mineral acid, not balanced by the ammonium ions formed during hydrolysis, must be neutralized before the glycolic acid can be recovered by economically sound procedures, and the crude glycolic acid solution contains large amounts of neutral salts. Recovery of pure glycolic acid from such solutions is costly.

Neither precipitation of calcium glycolate (U.S. Pat. No. 2,028,064) or of zinc glycolate (U.S. Pat. No. 2,686,797), nor steam distillation of glycolic acid from methyl-isobutylketone, nor conversion of glycolic acid to the lower alkyl esters and hydrolysis of the esters after separation from the aqueous residue of the hydrolysis mixture (U.S. Pat. No. 2,419,137) have found significant industrial application. They permit at best a recovery of 80% of the glycolic acid values originally present.

It has now been found that glycolic acid can be extracted practically completely and in pure form from the hydrolysis mixture by contact, preferably in counter-current flow, with an extraction medium consisting essentially of at least one trialkyl phosphate having up to six carbon atoms in its alkyl moieties with a dialkyl ether having alkyl moieties of two to five carbon atoms in a weight ratio of 10:90 to 90:10. Practically pure glycolic acid is obtained when the glycolic acid is separated from the extract, as by counter-current extraction with water.

The extraction with the ester-ether mixture is performed preferably after hydrolysis of glycolonitrile in the presence of amounts of sulfuric acid stoichiometrically equivalent to the glycolonitrile, that is, one mole of sulfuric acid per two moles of glycolonitrile so that the hydrolysis mixture consists essentially of the desired glycolic acid, neutral ammonium sulfate, and water. After removal of the glycolic acid by extraction, the ammonium sulfate may be recovered in a conventional manner in the form of practically colorless crystals directly useful for use in fertilizers or fire extinguishing compositions. The hydrolysis of glycolonitrile readily goes to completion when an excess of sulfuric acid is avoided.

Glycolonitrile is hydrolyzed by adding sulfuric acid to an aqueous solution of the nitrile and holding the mixture at elevated temperature. The concentration of the added sulfuric acid is chosen according to the amount of water in the nitrile solution. A 55% sulfuric acid solution is usually most economical, but concentrations between 40% and 80% may be employed in most cases to suit specific requirements. The hydrolysis is preferably performed at a boil at ambient pressure and requires 3 to 6 hours, depending on the concentration of the hydrolysis mixture and its boiling temperature which may vary between 100° and 150° C. A hydrolysis temperature of 135° to 140° C is representative of presently preferred practice. When hydrolysis is completed, no secondary, organic reaction products are formed even in the absence of catalysts, such as chloride ions.

The hydrolysis mixture is contacted with the extraction solvents until the glycolic acid is dissolved in the organic phase. Counter-current, multiple-stage extraction is preferred and may be carried out at ambient temperature or at elevated temperature. The distribution of glycolic acid in the two phases is most advantageous, and solvent losses to the aqueous phase are minimal if the extraction medium consists of equal weights of tributyl phosphate and diisopropyl ether, but very good results are obtained at ratios of 40:60 to 60:40, and solvent mixtures containing only 10% of one component are useful. The other trialkyl phosphates having up to six carbon atoms in their alkyl moieties and the other dialkyl ethers having two to five carbon atoms in theirs combine low cost, ready availability, low solubility in water, low volatility at ambient temperature, and other relevant desirable properties to a lesser extent than tributyl phosphate and isopropyl ether, although they are effective in the same proportions.

The manner in which glycolic acid is separated from the extraction medium depends mainly on the later use of the acid, and conventional procedures will readily suggest themselves. It is often advantageous to remove the glycolic acid from the extract by counter-current extraction with water which yields an aqueous solution of practically pure glycolic acid in amounts approaching 100% of the glycolic acid values in the hydrolysis mixture. Small amounts of dissolved trialkyl phosphate and dialkyl ether may be removed from the aqueous glycolic acid solution by steam distillation and returned to the process. The aqueous solution ultimately obtained may contain up to 20% glycolic acid by weight, is practically colorless and free from inorganic salts, particularly ammonium sulfate. Its concentration may be adjusted as needed by dilution or partial evaporation.

While the method of the invention can be carried out batchwise, continuous operation is preferred for manufacture of glycolic acid on an industrial scale. The following Example is further illustrative of this invention. All parts are by weight.

EXAMPLE

205 Parts 96% sulfuric acid were diluted with 200 parts water in the first stage of a four-stage cascade reactor, and the mixture was heated to about 100° C, whereupon 259 parts 88% aqueous glycolonitrile was added gradually with stirring over a period of approximately 10 minutes. The ensuing strongly exothermic hydrolysis reaction caused the mixture to boil, and a boiling temperature was maintained with refluxing after the initial reaction subsided. The mixture reached a stable boiling temperature of 137° C after about 2 hours, and this temperature was maintained for another 2½ hours. Additional amounts of the reactants were added to the first stage of the reactor as the hydrolysis proceeded.

The aqueous solution discharged from the reactor was cooled to 60°-70° C and diluted with 200 parts water to avoid crystallization. Analysis of the effluent showed 99% conversion of the nitrile to glycolic acid in the solution which was contaminated with ammonium sulfate. The glycolic acid was extracted from the aqueous mixture at 40°-50° C in continuous counter-current contact with four times its weight of a 1:1 mixture of tributyl phosphate and diisopropyl ether. After the ninth stage of the conventional multiple-stage extractor employed, the aqueous liquid contained 265 parts ammonium sulfate and less than 3.5 parts glycolic acid. The ammonium sulfate was recovered by crystallization at lower temperature and by partial evaporation of the mother liquor.

Almost equally favorable distributions of the glycolic acid between the aqueous and organic phases were achieved by extraction of the hydrolysis product with mixtures of tributyl phosphate and diisopropyl ether in respective weight ratios of 35:65 and 65:35.

The extract was contacted with approximately one tenth of its weight of water in a continuous, countercurrent extractor. Aqueous solutions containing 18% to 20% by weight of glycolic acid were obtained in several runs. The solutions were partly evaporated to remove the low-boiling diisopropyl ether and the tributyl phosphate which is volatile with the water vapor, and to recover 426.4 parts of a 70% aqueous solution of pure glycolic acid, corresponding to a 98.3% yield based on the hydrolyzed glycolonitrile.

It should be understood, of course, that the foregoing disclosure relates only to currently preferred practice in carrying out the invention, and that it is intended to cover all changes and modifications of the embodiments of the invention herein chosen for the purpose of the disclosure which do not constitute departures from the spirit and scope of the appended claims.

What is claimed is:

1. A method of recovering purified glycolic acid from an aqueous solution thereof contaminated with ammonium and sulfate ions in respective amounts at least stoichiometrically equivalent to said glycolic acid which comprises:

a. contacting said contaminated solution with an extraction medium consisting essentially of a mixture of a trialkyl phosphate with a dialkyl ether until said glycolic acid is dissolved in said extraction medium,
      1. alkyl in said trialkyl phosphate having up to six carbon atoms,
      2. alkyl in said dialkyl ether having two to five carbon atoms,
      3. each of said trialkyl phosphate and said dialkyl ether constituting at least 10% by weight of said medium; and
   b. separating said glycolic acid from said extraction medium.

2. A method as set forth in claim 1, wherein said contaminated solution, prior to said contacting is formed by hydrolyzing glycolonitrile in the presence of sulfuric acid, at elevated temperature, said glycolic acid being separated from said extraction medium by contacting said extraction medium with water until said glycolic acid is dissolved in said water.

3. A method as set forth in claim 2, wherein said elevated temperature is 100° to 150° C, and the amount of said sulfuric acid is approximately one mole for each 2 moles of said glycolonitrile.

4. A method as set forth in claim 3, wherein said extraction medium is contacted sequentially with said contaminated solution and with said water in countercurrent flow.

5. A method as set forth in claim 2, wherein said trialkyl phosphate is tributyl phosphate, and said dialkyl ether is diisopropyl ether.

6. A method as set forth in claim 5, wherein each of said tributyl phosphate and diisopropyl ether constitutes at least 35% by weight of said extraction mixture.

7. A method as set forth in claim 6, wherein said extraction mixture consists essentially of approximately equal weights of said tributyl phosphate and of said diisopropyl ether.

* * * * *